(12) United States Patent
Meier et al.

(10) Patent No.: US 7,690,257 B2
(45) Date of Patent: Apr. 6, 2010

(54) METHOD AND DEVICE FOR CHECKING A WELDING SEAM PRESENT AT ONE OF THE INTERIOR SURFACES OF A REACTOR PRESSURE VESSEL

(75) Inventors: Rainer Meier, Erlangen (DE); Thomas Rehfeldt, Möhrendorf (DE); Peter Kaluza, Bamberg (DE)

(73) Assignee: Intelligendt Systems & Services GmbH, Erlangen (DE)

( * ) Notice: Subject to any disclaimer, the term of this patent is extended or adjusted under 35 U.S.C. 154(b) by 268 days.

(21) Appl. No.: 11/799,064

(22) Filed: Apr. 30, 2007

(65) Prior Publication Data

US 2007/0253519 A1    Nov. 1, 2007

(30) Foreign Application Priority Data

Apr. 28, 2006    (DE) .................. 10 2006 020 352

(51) Int. Cl.
*G01N 29/00*    (2006.01)
*G21C 17/00*    (2006.01)

(52) U.S. Cl. ............................. 73/588; 73/601; 73/609; 73/622; 73/865.8; 376/249

(58) Field of Classification Search ................ 73/588, 73/622, 865.8, 579, 583, 587, 593, 601, 623, 73/627, 628, 629, 633, 634, 589, 600; 376/249, 376/245
See application file for complete search history.

(56) References Cited

U.S. PATENT DOCUMENTS

| | | | |
|---|---|---|---|
| 4,099,419 A * | 7/1978 | Kuroda et al. ................. 73/626 |
| 4,545,251 A * | 10/1985 | Uchida et al. ................. 73/631 |
| 5,156,803 A * | 10/1992 | Engding et al. ............. 376/249 |
| 5,267,481 A | 12/1993 | Smith |
| 5,460,045 A * | 10/1995 | Clark et al. ................... 73/622 |
| 5,571,968 A * | 11/1996 | Buckley ...................... 73/623 |

(Continued)

FOREIGN PATENT DOCUMENTS

EP    0 539 049 A1    4/1993

(Continued)

OTHER PUBLICATIONS

Author not named, "Bottom Mounted Instrument Penetration Condition Resolution", Nuclear Operating Company, dated Jul. 17, 2003, pp. 1-33.

*Primary Examiner*—J M Saint Surin
(74) *Attorney, Agent, or Firm*—Laurence A. Greenberg; Werner H. Stemer; Ralph E. Locher

(57) ABSTRACT

In a method and a device for testing a weld seam (8), located on the inner surface of a reactor pressure vessel (2), by which the outer circumference of an instrumentation nozzle (4) leading into the interior of this reactor pressure vessel (2) is welded onto the reactor pressure vessel (2), an ultrasound test probe (20) with a linear ultrasound transducer array (30) is inserted into the instrumentation nozzle (4), which ultrasound transducer array (30) is parallel to the central axis (12) of the instrumentation nozzle (4) in terms of its longitudinal direction, and is used to couple a transmitted ultrasound signal (S) into the instrumentation nozzle (4) in the region of the weld seam (8) and to receive a reflected ultrasound signal (R).

9 Claims, 3 Drawing Sheets

U.S. PATENT DOCUMENTS

| | | | |
|---|---|---|---|
| 6,169,776 B1 * | 1/2001 | Collins | 376/249 |
| 6,332,011 B1 * | 12/2001 | Johnson | 376/249 |
| 6,848,313 B2 | 2/2005 | Krieg et al. | |
| 6,865,243 B2 * | 3/2005 | Paillaman et al. | 376/245 |
| 6,886,407 B1 * | 5/2005 | Fredenberg | 73/622 |
| 6,904,817 B2 * | 6/2005 | Davis et al. | 73/865.8 |
| 7,134,352 B2 * | 11/2006 | Davis et al. | 73/865.8 |
| 7,412,890 B1 * | 8/2008 | Johnson et al. | 73/618 |
| 7,428,842 B2 * | 9/2008 | Fair et al. | 73/626 |
| 2003/0136195 A1 | 7/2003 | Krieg et al. | |
| 2004/0091076 A1 | 5/2004 | Kerr et al. | |

FOREIGN PATENT DOCUMENTS

| | | |
|---|---|---|
| EP | 0 619 489 A1 | 10/1994 |
| EP | 1 415 731 A2 | 5/2001 |
| EP | 1 333 277 A2 | 8/2003 |

* cited by examiner

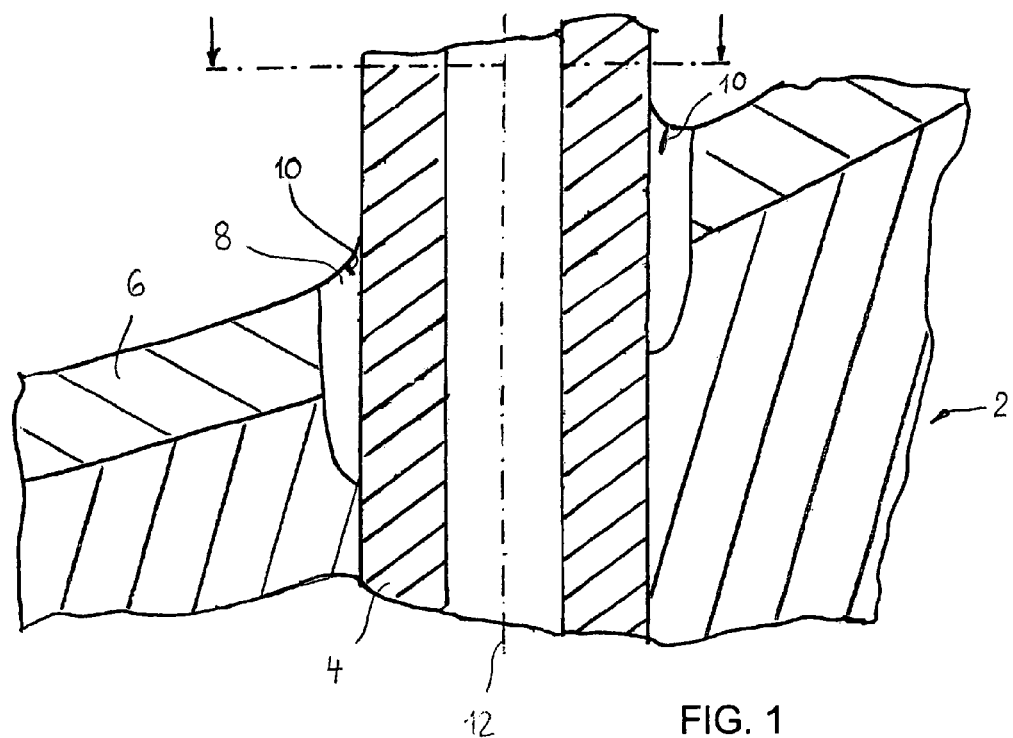
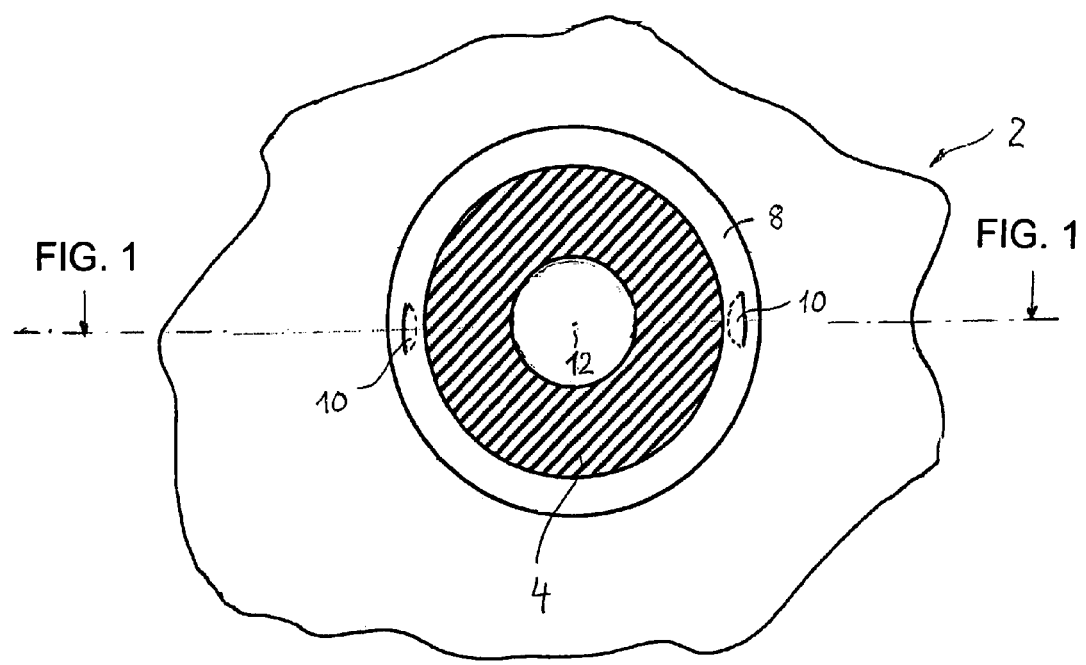

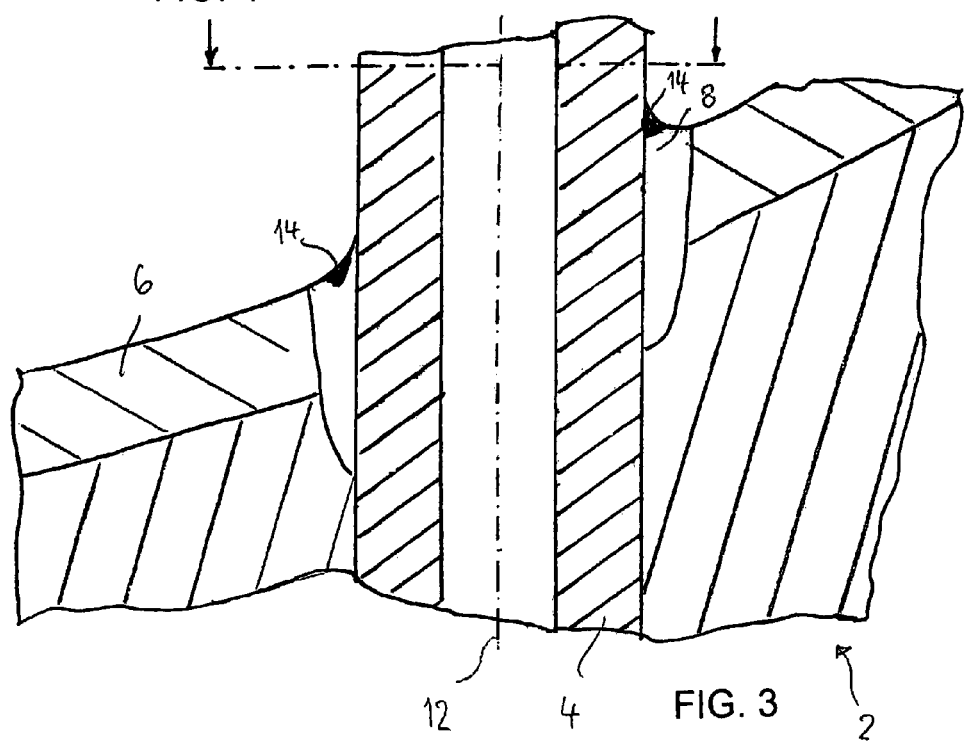
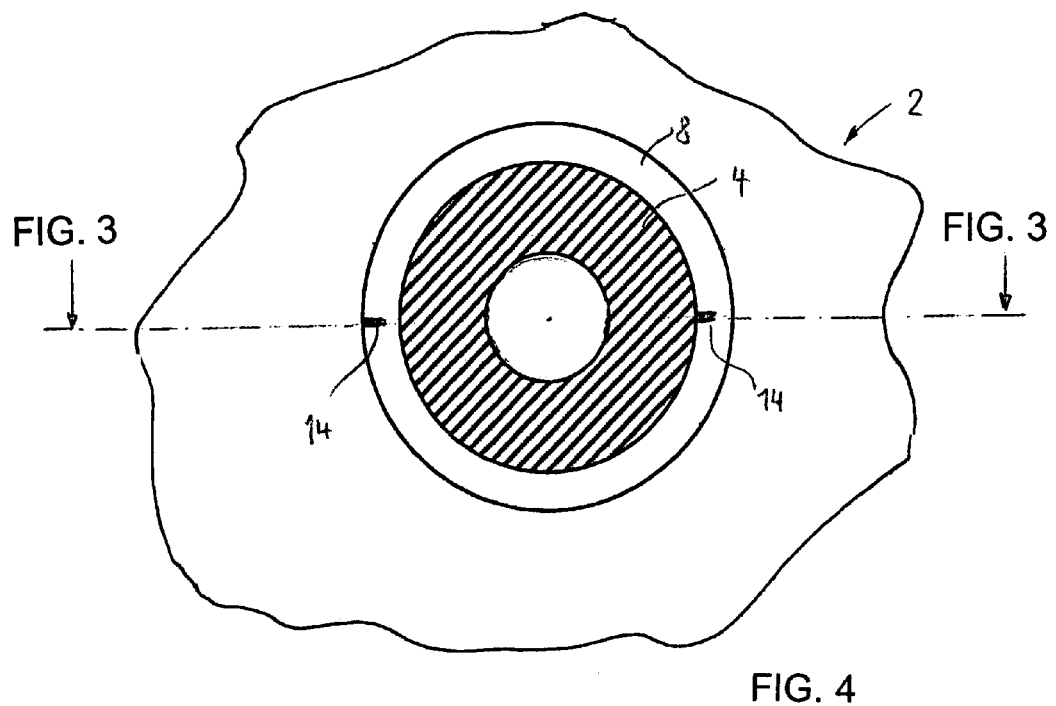

METHOD AND DEVICE FOR CHECKING A WELDING SEAM PRESENT AT ONE OF THE INTERIOR SURFACES OF A REACTOR PRESSURE VESSEL

BACKGROUND OF THE INVENTION

Field of the Invention

The invention relates to a method and a device for testing a weld seam, located on the inner surface of a reactor pressure vessel of a nuclear reactor, by which the outer circumference of an instrumentation nozzle leading into the interior of the reactor pressure vessel is welded onto the reactor pressure vessel.

The reactor pressure vessels of pressurized water reactors are frequently provided with bushings on their lower head (bottom head), by means of which bushings the core instrumentation probes are inserted from the outside into the reactor pressure vessel. These bushings or instrumentation nozzles (LCIP=Lower Core Instrumentation Penetration) are produced from a forged rod with a hole through it, and are welded in by means of a weld seam which is located inside the reactor pressure vessel and runs around their outer circumference in an annular fashion. Particularly in older systems, the bushings, the weld filler and the buffer weld, which is applied on the inner surface of the reactor pressure vessel, use materials which have been found to be particularly susceptible to stress corrosion cracking. In this case, stress corrosion cracking is a corrosion process which occurs in the vicinity of water on components which have internal stresses.

The weld seam is usually designed as a "J-groove weld" and ends, toward the instrumentation nozzle, in a fillet. The geometry of the weld seam is in this case dependent on the position of the instrumentation nozzle on the bottom head. By way of example, the weld seam, by which an instrumentation nozzle is welded on in the center of the bottom head, has a contour which is rotationally symmetrical about the central axis of the instrumentation nozzle, whereas the contour of the weld seam of an instrumentation nozzle which is welded on at the edge of the bottom head is asymmetric.

Since the weld seams are susceptible to stress corrosion cracking, they need to be inspected at regular intervals. Owing to the complexity of the test problem, which is caused in particular by the asymmetric contour of the weld seam, this inspection is generally carried out only visually using a video camera, which is introduced into the reactor pressure vessel. To this end, the fuel assemblies need to be unloaded prior to this. In the course of such a visual inspection, however, it is possible to identify only cracks which have already reached a considerable size. As an alternative to such a visual inspection, an attempt has been made to inspect the weld seams using an eddy current testing probe (http://www.nrc.gov.edgesuite.net/reactors/operating/op s-experience/pressure-boundary-integrity/bottom-head-issues/bottom-head-files/july-17-nrc.pdf). This is made more difficult, however, by the irregular surface geometry of the weld seam. Additionally, in the case of an eddy current test, the determination of the crack depth is restricted by the skin effect. Further, it is also necessary in this case for the core to be completely unloaded.

It is known from U.S. Pat. No. 5,460,045 to test the weld seam of an instrumentation nozzle of a boiling water reactor, which nozzle is newly inserted in the course of repair measures, using an ultrasound test probe which can be moved into the interior of the instrumentation nozzle. Depending on the objective of the test, the ultrasound test probe contains five or nine ultrasound transducers which are aligned such that both crack faults which run in the circumferential direction and those which are aligned in the radial direction can be identified. In order to identify crack faults which are aligned in the circumferential direction, at least two ultrasound transducers are provided which are axially spaced apart from one another and produce ultrasound signals which each propagate at an angle to the longitudinal axis of the probe. One ultrasound transducer produces a radially propagating ultrasound signal and two further ultrasound transducers produce an ultrasound signal which propagates at a right angle to the axial direction in the clockwise or counterclockwise direction. In order to inspect the annularly peripheral weld seam, an ultrasound test probe with five ultrasound transducers is used.

An ultrasound test probe with five differently aligned ultrasound transducers, which can be inserted into a pipe nozzle, is also known from EP 0 539 049 A1. In this known embodiment, all the ultrasound transducers are arranged on a single plane which is aligned at a right angle to the longitudinal axis of the ultrasound test probe.

SUMMARY OF THE INVENTION

The invention is now based on the object of providing a method which can be used to test, with great reliability and detection sensitivity, a weld seam which is located on the inner surface of a reactor pressure vessel and can be used to weld the outer circumference of an instrumentation nozzle leading into the interior of said reactor pressure vessel onto the reactor pressure vessel. The invention is further based on the object of providing a device which is suitable for carrying out this method.

As regards the method, the stated object is achieved according to the invention by virtue of a method with the features of patent claim 1. In this method, an ultrasound test probe is inserted into the instrumentation nozzle and is used to couple an ultrasound signal into the instrumentation nozzle in the region of the weld seam and to receive a reflected ultrasound signal.

The invention is based here on the consideration that the sensitivity with which a crack fault can be detected is improved considerably with respect to the methods known in the prior art by coupling an ultrasound signal into the weld seam starting from the inner face of the instrumentation nozzle on account of the simple geometric conditions prevailing on the inner surface of the instrumentation nozzle.

Moreover, the complexity for guiding the ultrasound test probe is simplified since the latter can be moved without problems inside the instrumentation nozzle on the inner surface in its circumferential direction and in its axial direction by means of a rotational movement or an axial translatory movement and does not have to be guided on a complex weld seam surface.

Since the weld seam is tested starting from the inner surface of the instrumentation nozzle, it is also possible in principle to carry out the test without unloading the fuel assemblies from the reactor pressure vessel for this purpose.

Since the transmitted ultrasound signal propagates inside the instrumentation nozzle at an oblique angle, i.e. at an angle to the central axis, even crack faults which extend at an angle to this central axis and are located in the region of the weld seam surface can be detected with high detection sensitivity.

Since, for the purposes of producing the ultrasound signal, an ultrasound transducer array is additionally used which is constructed from a plurality of transducer elements arranged one next to one another in a longitudinal direction and is arranged parallel to the central axis in terms of its longitudinal direction and whose transducer elements are actuated with a time delay with respect to one another for adjusting the angle at which the ultrasound signal propagates inside the instrumentation nozzle in relation to the central axis, a particularly good detectability of crack faults which extend with different inclinations at an angle to the central axis is achieved.

Moreover, the ultrasound signal can be focussed additionally at different depths of focus by means of corresponding actuation of the transducer elements with a time delay. This achieves particularly high test sensitivity for crack faults located at this depth of focus.

In an advantageous refinement of the method, the transmitted ultrasound signal propagates inside the instrumentation nozzle on a plane which is parallel to and spaced apart from the central axis of the instrumentation nozzle. In other words, the ultrasound signal is transmitted inside the instrumentation nozzle in such a direction that the projection of its propagation direction onto a plane, which extends at a right angle to the central axis of the instrumentation nozzle and through the point of incidence of the ultrasound signal on the inner surface, assumes an angle, which is different from zero, to the normal which is at a right angle to the inner surface at the point of ensonification or of incidence. These measures can be used to detect cracks which extend both axially and radially in the weld seam particularly well. The method is carried out in particular with at least one ultrasound transducer array operated according to a pulse-echo technique.

An additionally improved assessment of the received reflected ultrasound signals is possible if an ultrasound transducer arrangement, which has at least two ultrasound transducer arrays and can be operated according to a transmitting/receiving technique, is used, with the ultrasound transducer arrays being arranged in a fashion spaced apart from one another and mirror-symmetric to a plane containing the central axis. Such an arrangement can be used in particular to detect crack faults which extend in the circumferential direction with particular reliability.

In a further preferred refinement of the invention, transverse waves are used for the transmitted ultrasound signal. As a result, in particular the traceability of cracks which extend radially and in the axial direction is improved.

As regards the device, the object is achieved by virtue of a device having the features of patent claim 6 whose advantages, and also the advantages of its subordinate subclaims, correspond analogously to the advantages stated for the associated method claims.

For the purposes of explaining the invention in further detail, reference is made to the exemplary embodiments of the drawing, in which:

BRIEF DESCRIPTION OF THE SEVERAL VIEWS OF THE DRAWING

FIGS. 1 and 3 each show a partial longitudinal section through the bottom head of a reactor pressure vessel with an instrumentation nozzle welded therein with crack faults which each have different alignments, FIGS. 2 and 4 show the cross section (associated with FIGS. 1 and 3) through the instrumentation nozzle, in which the weld seam is reproduced in each case in a plan view.

DESCRIPTION OF THE INVENTION

Figure 5:
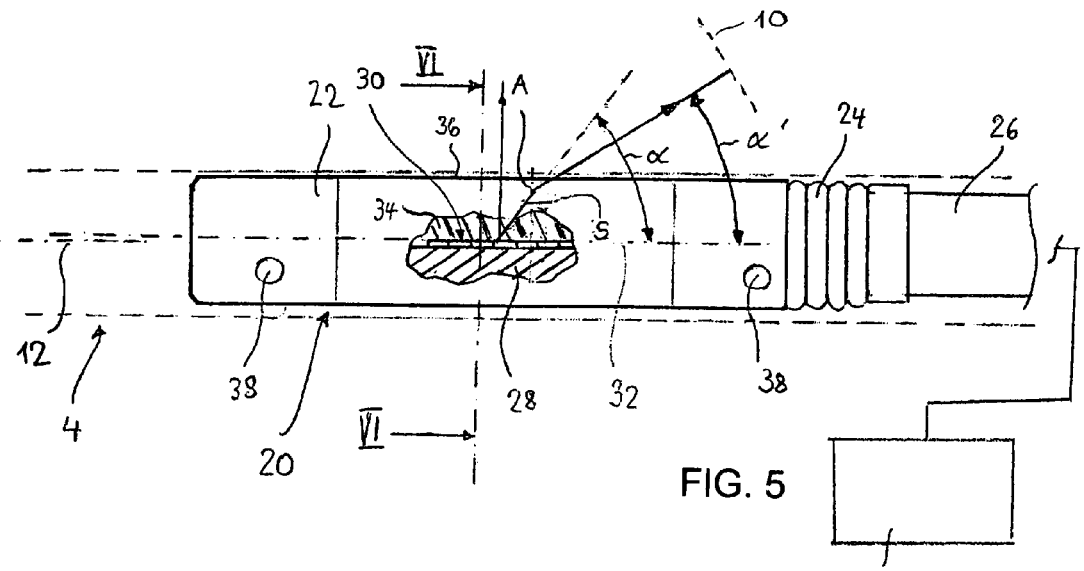
FIG. 5 shows a side view of a test probe in accordance with the invention with a partial longitudinal section.

In accordance with FIGS. 1 and 2, a hollow cylindrical instrumentation nozzle 4 leading into the interior of a reactor pressure vessel 2 is arranged in the bottom head of the reactor pressure vessel 2. On its inner surface, the reactor pressure vessel 2 is provided with a buffer weld 6 or weld plating made of Inconel or stainless steel. The instrumentation nozzle 4 is welded in on this inner surface with a weld seam 8, which annularly surrounds the nozzle, using a weld filler made of Inconel.

In the illustrated example this weld seam 8 now has crack faults 10 which start from the free surface of the weld seam 8, which surface has the shape of a hollow fillet, and extend into the interior of the weld seam 8 at an angle to the central axis 12 of the instrumentation nozzle 4. These crack faults extend on the surface approximately in the circumferential direction and have the shape of a half ellipse, as can be seen from the dashed illustration of FIG. 2.

The example of FIGS. 3 and 4 illustrates plane crack faults 14 which likewise start from the free surface of the weld seam and, unlike the crack faults 10 illustrated in FIGS. 1 and 2, are aligned substantially radially to the central axis 12.

In accordance with FIG. 5, a device in accordance with the invention comprises an ultrasound test probe 20 which can be inserted into the interior of an instrumentation nozzle 4, whose inner wall is illustrated only with dashed lines in the figure, and whose outside diameter is only slightly smaller than the internal diameter of the instrumentation nozzle 4. The ultrasound test probe 20 comprises a cylindrical probe head 22, which is attached via a bellows 24 to an advancing rod or a flexible advancing tube 26, by means of which it can be inserted into the instrumentation nozzle 4 and be advanced therein up to the height of the weld seam. It is also possible to provide a universally jointed hinge rather than a bellows 24 for the purposes of a flexible coupling between the advancing rod 26 and probe head 22.

A linear ultrasound transducer array 30 is arranged in the probe head 22 on a damping body (backing) 28 such that its transmission face is situated approximately in a plane containing the longitudinal axis 32 of the probe head 22. The linear ultrasound transducer array 30 is constructed from a plurality of transducer elements arranged next to one another in a longitudinal direction and is arranged parallel to the longitudinal axis 32 of the probe head 22 in terms of its longitudinal direction.

The ultrasound transducer array 30 is embedded in a half-cylindrical lead body 34 made of PMMA, whose surface, which faces away from the ultrasound transducer 30, is simultaneously used as a cylindrical coupling face 36 which is brought to bear on the inner surface of the instrumentation nozzle 4. In order to achieve coupling which is as gap-free as possible, a plurality of, in the exemplary embodiment four, knob-like supporting elements 38, which are resiliently supported on the inner surface of the instrumentation nozzle 4 and press the coupling face 36 onto the inner surface of the instrumentation nozzle 4, which faces away from the supporting elements 38, are arranged on the face of the probe head 22, which faces away from the coupling face 36.

The ultrasound test probe 20 is connected to a control and evaluation device 40, which is only schematically indicated in the figure and can be used to actuate the individual transducer elements with a time delay such that the ultrasound signal S which is transmitted by the ultrasound transducer 30 and is preferably a transverse wave propagates inside the ultrasound test probe 20 at an angle to its longitudinal axis 32 and thus also at an angle to the central axis 12 of the instrumentation nozzle 4, which virtually coincides with the longitudinal axis 32. The transmitted ultrasound signal S then strikes the inner surface of the instrumentation nozzle 4 at an oblique angle α and is additionally refracted during the transition into the instrumentation nozzle 4 toward the longitudinal axis 32, with the result that it propagates at an oblique angle α', which is smaller than the oblique angle α, in the instrumentation nozzle 4 toward the weld seam. In this manner, crack faults 10 which are aligned at an angle to the longitudinal axis 32 or to the central axis 12 can be reliably detected using an ultrasound transducer 30, which is operated according to the pulse-echo method. In the illustrated example, the angle α' is adjusted such that the transmitted ultrasound signal S strikes an interface formed by the crack fault 10 at a right angle and is reflected back on itself, with the result that it is received in the receiving operation by the transducer elements which are actuated with a time delay according to the transmission operation.

Figure 6:
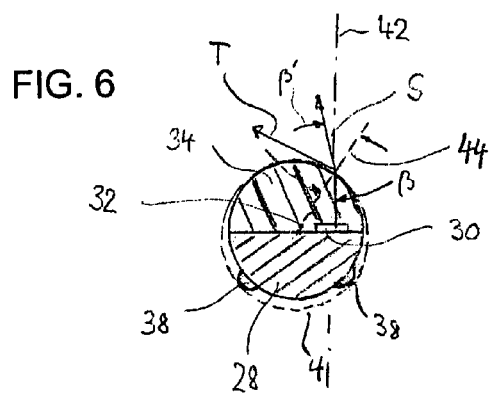
FIG. 6 shows a cross section through the test probe, and FIGS. 7 and 8 each show an alternative embodiment of the ultrasound test probe in accordance with the invention likewise in a schematic cross section.

FIG. 6 shows that the linear ultrasound transducer array 30, which is aligned at a right angle to the plane of the drawing in terms of its longitudinal axis, is also arranged with a lateral offset to the longitudinal axis 32 of the ultrasound test probe 20 such that its transmission axis, which is at a right angle to the transmission face in the centroid of this transmission face in the case of actuation of all the transducer elements without time delay, is arranged spaced apart from the central axis 12 (not drawn in the figure for reasons of clarity) of the instrumentation nozzle 4, which central axis is arranged offset only slightly with respect to the longitudinal axis 32 in the case that the ultrasound test probe 20 is inserted into the instrumentation nozzle 4. The transmitted ultrasound signal S then propagates inside the ultrasound test probe 20 in a plane 42 which is parallel to and spaced apart from the longitudinal axis 32 of the ultrasound test probe 20 and thus also from the central axis 12 of the instrumentation nozzle 4. An ultrasound signal S (all the transducer elements are actuated simultaneously), which propagates at a right angle to this longitudinal axis 32 in the direction of this transmission axis, then assumes, at the point of incidence A, an angle β, which is different from zero, to the normal 44 which is at a right angle in this point of incidence A to the inner surface, with the result that, as it enters the instrumentation nozzle 4, it is refracted away from this normal 44 and propagates there at an angle $β'>β$ with respect to said normal 44. In other words, the ultrasound signal S produced in the instrumentation nozzle 4 has a component T which is tangential to its circumference and is aligned, in the illustrated exemplary embodiment, counterclockwise. In the case of an ultrasound signal S propagating in the plane 42 at an angle to the longitudinal axis 32, i.e. with a direction component at a right angle to the plane of the drawing, the non-central arrangement of the ultrasound transducer array 30 accordingly has the effect that the projection of the propagation direction of the transmitted ultrasound signal S onto a plane, which extends at a right angle to the central axis 12 of the instrumentation nozzle 4 and through the point of incidence A of the ultrasound signal on the inner surface, assumes an angle β, which is different from zero, to the normal 44 which is at a right angle at the point of incidence A on the inner surface.

Figure 7:
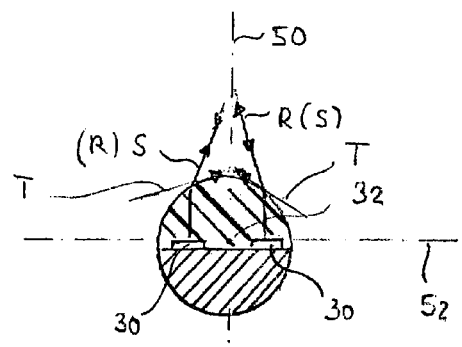

In the exemplary embodiment of FIG. 7, two ultrasound transducer arrays 30 are provided, which are arranged next to one another and can be operated both by themselves in the pulse-echo operation and in the transmitting/receiving operation, in the case of which one of the ultrasound transducer arrays 30 transmits an ultrasound signal S and the other one of the ultrasound transducer arrays 30 receives a reflected ultrasound signal R. The ultrasound transducer arrays 30 are mirror-symmetric to a plane 50, which contains the longitudinal axis 32 and extends at a right angle to the plane of the drawing, in a shared plane 52, which likewise contains the longitudinal axis 32, i.e. with transmission faces which extend parallel to one another in this plane 52, with the result that they produce ultrasound signals S in the instrumentation nozzle 4, whose propagation directions in the instrumentation nozzle have components T, which are tangential to its circumference and are aligned in the opposite direction with respect to each other, i.e. clockwise and counterclockwise. These measures can be used to ensonify cracks from opposite directions in the pulse-echo operation. This increases the likelihood of finding the cracks. If the ultrasound transducer arrays 30 are operated in the transmitting/receiving operation, cracks which are aligned in the circumferential direction about the instrumentation nozzle can be found here particularly well.

Figure 8:
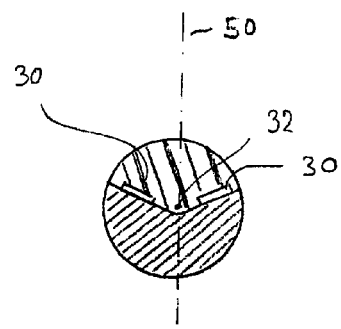

In the exemplary embodiment according to FIG. 8, the ultrasound transducer arrays 30 are likewise arranged in a fashion mirror-symmetric to a plane 50 containing the longitudinal axis 32, but at an inclination with respect to one another, in order to thus enable in the transmitting/receiving operation an additional adjustment of the propagation conditions to the distance between a crack fault extending in the circumferential direction and the inner surface of the instrumentation nozzle. In the case of the inclination which is illustrated in an exaggerated manner in the example of the figure, in which the transmission faces face each other, crack faults can be detected which are situated closer to the inner surface.

LIST OF REFERENCE SYMBOLS 2 reactor pressure vessel
4 instrumentation nozzle
6 buffer weld
8 weld seam
10, 14 crack fault
12 central axis
20 ultrasound test probe
22 probe head
24 bellows
26 advancing rod
28 backing
30 ultrasound transducer array
32 longitudinal axis
34 lead body
36 coupling face
38 supporting element
40 control and evaluation device
42 plane
44 normal
50, 52 plane
A point of incidence
S, R transmitted, reflected ultrasound signal
T tangential component
α, β angles

The invention claimed is:

1. A method for testing a weld seam located on an inner surface of a reactor pressure vessel and connecting an outer circumference of an instrumentation nozzle leading into an interior of the reactor pressure vessel to the reactor pressure vessel, the method which comprises:

inserting an ultrasound test probe into the instrumentation nozzle, coupling a transmitted ultrasound signal into the instrumentation nozzle in a region of the weld seam and receiving a reflected ultrasound signal with the ultrasound test probe for determining a presence of faults in the weld seam;

generating the ultrasound signal with at least one linear ultrasound transducer array constructed from a plurality of transducer elements arranged next to one another in a longitudinal direction, the transducer array having a longitudinal direction extending parallel to the central axis; and causing the transmitted ultrasound signal to propagate inside the instrumentation nozzle at an oblique angle to the central axis of the instrumentation nozzle by actuating the transducer elements of the transducer array with a time delay with respect to one another for adjusting the oblique angle.

2. The method according to claim 1, which comprises causing the transmitted ultrasound signal to propagate inside the instrumentation nozzle on a plane parallel to and spaced apart from the central axis of the instrumentation nozzle.

3. The method according to claim 1, which comprises operating the at least one ultrasound transducer array according to a pulse-echo technique.

4. The method according to claim 1, which comprises providing an ultrasound transducer assembly operable according to a transmitting/receiving technique and containing at least two ultrasound transducer arrays that are spaced apart from one another and mirror-symmetric to a plane containing the central axis.

5. The method according to claim 1, which comprises utilizing transverse waves for the transmitted ultrasound signal.

6. A device for testing a weld seam, located on an inner surface of a reactor pressure vessel, by which an outer circumference of an instrumentation nozzle leading into the reactor pressure vessel is welded onto the reactor pressure vessel, the device comprising:

an ultrasound test probe configured for insertion into the instrumentation nozzle, said test probe having a longitudinal axis;

at least one linear ultrasound transducer array formed with a plurality of transducer elements disposed next to one another in a longitudinal direction, said transducer array being disposed, in terms of the longitudinal direction, parallel to said longitudinal axis of said test probe inside said test probe;

a control and evaluation device connected to said transducer array for actuating said transducer elements with a time delay; and wherein a transmission axis of said transducer elements is spaced apart from a central axis of the instrumentation nozzle when said ultrasound test probe is inserted in the instrumentation nozzle.

7. The device according to claim 6, wherein at least one linear ultrasound transducer array is one of at least two ultrasound transducer arrays disposed spaced apart from one another and mirror-symmetric to a plane containing said longitudinal axis of said ultrasound test probe, and wherein at least one of said at least two ultrasound transducer arrays is a transmitter and the other one is a receiver.

8. The device according to claim 6, wherein said ultrasound test probe is formed with a cylindrical coupling face, wherein at least one supporting element is disposed on a side facing away from said coupling face of said ultrasound test probe, and wherein said supporting element is resiliently supported on an inner surface of the instrumentation nozzle, when said ultrasound test probe is inserted in the instrumentation nozzle, and presses said coupling face onto the inner surface of the instrumentation nozzle.

9. The device according to claim 6, wherein said ultrasound transducer array is configured to produce transverse waves.

\* \* \* \* \*